(12) United States Patent
Schmenger et al.

(10) Patent No.: US 7,670,391 B2
(45) Date of Patent: *Mar. 2, 2010

(54) DYE-CONTAINING PELLETS FOR COLORING KERATIN FIBERS

(75) Inventors: Juergen Schmenger, Weiterstadt (DE); Petra Braun, Muenster (DE); Wolfram Englisch, Bannewitz (DE)

(73) Assignee: Wella AG, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/103,392

(22) Filed: Apr. 15, 2008

(65) Prior Publication Data

US 2009/0056039 A1   Mar. 5, 2009

Related U.S. Application Data

(63) Continuation of application No. 10/541,104, filed as application No. PCT/EP2004/004632 on May 3, 2004, now Pat. No. 7,458,992.

(30) Foreign Application Priority Data

Oct. 10, 2003 (DE) ................................ 103 47 242

(51) Int. Cl.
  *A61Q 5/10* (2006.01)

(52) U.S. Cl. .......... 8/405; 8/406; 8/407; 8/411; 8/435; 8/456; 8/463; 8/526; 8/552; 8/553; 8/559

(58) Field of Classification Search ............. 8/405, 8/406, 407, 411, 435, 456, 463, 526, 552, 8/553, 559
See application file for complete search history.

(56) References Cited

U.S. PATENT DOCUMENTS 5,017,195 A * 5/1991 Satou et al. .......... 8/526
7,458,992 B2 * 12/2008 Schmenger et al. ........ 8/405

* cited by examiner

*Primary Examiner*—Eisa B Elhilo
(74) *Attorney, Agent, or Firm*—Michael J. Striker

(57) ABSTRACT

The dust-free coated dye-containing pellet is a granulated carrier material that is encapsulated with a dye-containing coating material. The dye-containing coating material contains a mixture of a water-soluble or water-dispersible film-former with at least one direct dye and/or at least one oxidation dye precursor. Preferred carrier materials include dextrose, oligosaccharides and cellulose compounds. The dust-free coated dye-containing pellet is preferably made by granulating the carrier material together with optional antioxidants and auxiliary agents, heating the resulting granulate at no more than 34° C., subsequently coating the granulate by spraying it with a solution or dispersion of the coating material and optionally drying as needed.

11 Claims, 2 Drawing Sheets

DYE-CONTAINING PELLETS FOR COLORING KERATIN FIBERS

CROSS-REFERENCE

This is a continuation, filed under 35 U.S.C. 120, of U.S. patent application Ser. No. 10/541,104, which was filed on Jun. 30, 2005 now U.S. Pat. No. 7,458,992 and is the U.S. National Stage of PCT/EP 04/004632, which was filed on May 3, 2004 in the European Patent Office.

BACKGROUND OF THE INVENTION

1. The Field of the Invention

The present invention concerns dye-containing pellets obtained by a special method of preparation, as well as the use of these pellets for coloring keratin fibers.

2. The Related Art

Direct dyes, nitro dyes and pigment dyes or oxidation dyes in the form of colorless developer/coupler precursors are the dyes usually employed for the coloring of keratin fibers.

Dyes prepared according to the prior art are sold in conventional application forms. These application forms vary from liquid to creamy to waxy products. Aerosols, for example foam hair dyes, are also in use. According to the prior art, powdered dyes that must be mixed with an aqueous medium before use are also on the market.

The aforesaid agents, however, are not satisfactory in every respect. For example, in the case of oil-treated, dust-free powders, the oils used have an adverse effect on product performance, whereas when reactive dyes and raw materials are used as well as in the case of powders and liquid systems, problems arise in terms of storage stability.

BRIEF SUMMARY OF THE INVENTION

Surprisingly, we were able, by means of a suitable method that is carried out with the aid of suitable carrier and encapsulation (coating) materials, to develop a dye-containing pellet for coloring keratin fibers which does not have the aforedescribed drawbacks and, in addition, provides better dosability and multicolor effects.

Hence, the object of the present patent application is a dye-containing pellet which is obtained by (a) homogeneous mixing of a starting material containing at least one natural and/or synthetic dye with a suitable carrier material and then coating with a suitable encapsulation material or (b) coating a suitable carrier material with a mixture of at least one natural and/or synthetic dye and at least one suitable encapsulation material.

BRIEF DESCRIPTION OF THE DRAWING

The objects, features and advantages of the invention will now be illustrated in more detail with the aid of the following description of the preferred embodiments, with reference to the accompanying figures in which.

DETAILED DESCRIPTION OF THE INVENTION

Figure 1:
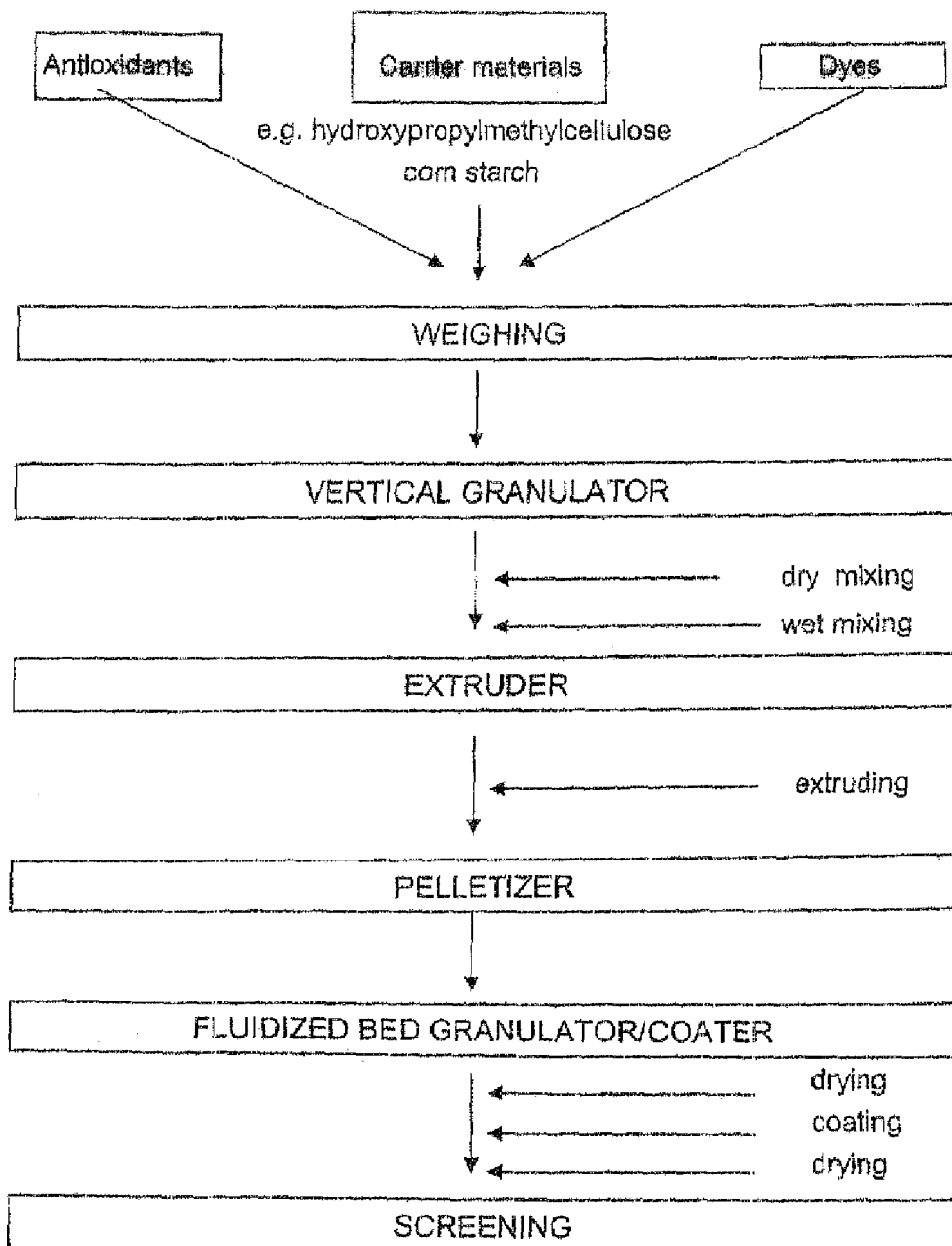
FIG. 1 is a flow chart showing an embodiment of a process based on extruder technology for preparing the coated dye-containing pellets according to the invention.
Figure 2:
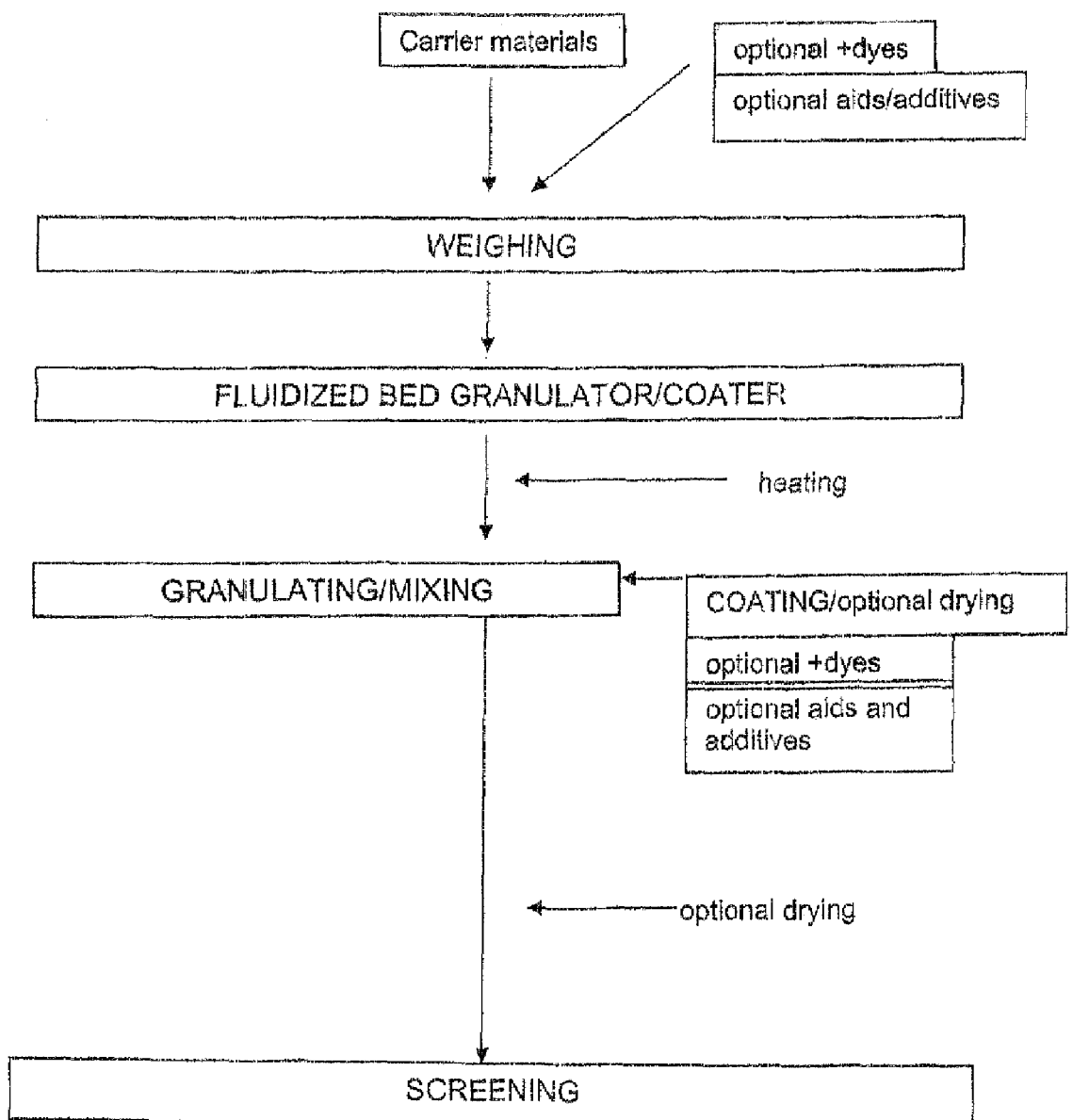
FIG. 2 is a flow chart showing an embodiment of a top spray process for preparing the coated dye-containing pellets according to the invention.

The dye-containing pellets of the invention are prepared by the process based on extruder technology and schematically shown in FIG. 1 [pellets as under (a)] or by the top spray process [pellets as under (a) or (b)] schematically presented in FIG. 2.

1. Preparation Based on Extruder Technology

A base composition is prepared in a vertical granulator (rotor rotational speed=50 to 200 rpm and preferably about 150 rpm; chopper rotational speed=750 to 1250 rpm and preferably about 1000 rpm) at room temperature (15 to 35° C.) by dry mixing and then wet mixing the dye composition with a carrier material and, optionally, antioxidants and other auxiliary agents. This base composition is then extruded from an extruder (rotational speed=15 to 50 rpm and preferably about 25 to 30 rpm; screen mesh size=about 0.01 to 5 mm, preferably 0.1 to 3 mm and particularly 0.6 to 1 mm). The resulting granulate is rounded in a pelletizer (rotational speed=400 to 800 rpm and preferably about 500 to 600 rpm). The granulate is then dried at a product temperature of 20 to 60° C. (preferably 30 to 55° C.) (incoming air temperature preferably about 70 to 80° C.) and then (optionally after previous warming to 40-50° C.) coated by the fluidized bed process (spraying rate preferably about 5 to 20 g/min; spraying air pressure preferably about 1.5 to 2.5 bar), the quantity of encapsulation material (based on the quantity of granulate to be coated) amounting to 0.5 to 50 weight percent, preferably 1 to 20 weight percent and particularly 2 to 15 weight percent. The product is finally dried (maximum product temperature about 51° C.).

2. Preparation by the Top Spray Process (a) By this process, the dye composition is mixed with the carrier materials and optionally with antioxidants and other auxiliary agents in a fluidized bed granulator/coater (rotor rotational speed=50 to 200 rpm and preferably about 150 rpm); chopper rotational speed=750 to 1250 rpm and preferably about 1000 rpm) at room temperature (15 to 35° C.). The base composition thus obtained is then heated (maximum product temperature about 34° C.), then granulated and finally coated (spraying rate preferably about 6 to 20 g/min; spraying air pressure preferably about 0.25 to 0.75 bar), the quantity of encapsulation material used (based on the quantity of the granulate to be coated) amounting to 0.5 to 50 weight percent, preferably 1 to 20 weight percent and particularly 2 to 10 weight percent. If necessary, the product is then dried (maximum product temperature about 60° C.).

(b) The carrier materials and optionally the antioxidants and other auxiliary agents are mixed with one another in a fluidized bed granulator/coater (rotor rotational speed=50 to 200 rpm and preferably about 150 rpm; chopper rotational speed=750 to 1250 rpm and preferably about 1000 rpm) at room temperature (15 to 35° C.). The base composition thus obtained is then heated (maximum product temperature about 34° C.), then granulated and finally coated with a solution/dispersion of the dyes in a suitable encapsulation material (spraying rate preferably about 6 to 20 g/min; spraying air pressure preferably 0.25 to 0.75 bar), the quantity of encapsulation material used (based on the quantity of granulate to be coated) amounting to 0.5 to 50 weight percent, preferably 1 to 20 weight percent and particularly 2 to 10 weight percent. If necessary, the product is then dried (maximum product temperature about 57° C.).

Suitable carrier materials for the dye-containing pellets are powdered, microcrystalline substances which place the dye in a physical state that allows the process for the coating of the pellets with suitable encapsulation materials to be carried out. Suitable carrier materials are, in particular, polyvinylpyrrolidone, dextrose, oligosaccharides, microcrystalline cellulose derivatives, for example hydroxypropylmethylcellulose, methylcellulose, hydroxyethylcellulose, hydroxypropyl-cellulose, nonoxynol-hydroxyethylcellulose and cetylhydroxyethylcellulose, or physically or chemically modified starches or starch derivatives, for example starch esters (for example acetylated starches), starch ethers (for example hydroxyalkylated starches), dialdehyde starches, dicarboxylstarches, distarch phosphates, hydroxyalkylstarch phosphates or hydroxyalkyl starches, wherein the alkyl groups preferably contain from 1 to 4 and more preferably 2 to 3 carbon atoms. Also suitable are crosslinked starch ethers, for example those bearing the INCI designations dimethylimidazolidone rice or corn starch, or hydrophobically modified starches (for example those bearing the INCI designation aluminum starch octenesuccinates). The starch can be modified thermally, hydrolytically or enzymatically, the starting starch possibly being obtained from known sources, for example corn, potatoes, sweet potatoes, peas, bananas, oats, wheat, barley, rice, sage, tapioca, taproot, amaranth, canna, sorghum etc. Particularly preferred starch derivatives are the nonionic starch derivatives, particularly the nonionic starch derivatives modified with an alkylene oxide such as ethylene oxide, propylene oxide or butylene oxide, or with acetic anhydride or butyl ketene dimer, and particularly with propylene oxide. Other suitable carrier materials are synthetic calcium silicate, diatomite, silicone dioxide or other free-flowing, non-caking powders.

Suitable encapsulation materials for the pellets of the invention are water-soluble or water-dispersible, film-forming substances which when spray-dried from solutions or dispersions are capable of depositing uniform films so that one can speak about encasing (coating). Suitable encapsulation materials are cellulose derivatives (for example methylcelluloses), polyethylene dispersions, polyacrylic acids, polyvinyl alcohols, polycarbonates, polyvinylpyrrolidone, polyesters and polyamides or natural film-formers, for example chitosan, shellac, oligosaccharides or Chinese balsam resin (colophony).

Suitable oxidation dye precursors are, for example, the following developers, couplers and self-coupling substances.

(i) Developers: 1,4-diaminobenzene (p-phenylenediamine), 1,4-diamino-2-methyl-benzene (p-toluoylenediamine), 1,4-diamino-2,6-dimethylbenzene, 1,4-diamino-3,5-diethyl-benzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)-benzene, 1,4-diamino-2-(pyridin-3-yl)benzene, 2,5-diaminobiphenyl, 1,4-diamino-2-methoxymethylbenzene, 1,4-diamino-2-aminomethylbenzene, 1,4-diamino-2-hydroxy-methyl-benzene, 1,4-diamino-2-(2-hydroxyethoxy)benzene, 2-[2-(acetylamino)ethoxy]-1,4-diamino-benzene, 4-phenylaminoaniline, 4-dimethylaminoaniline, 4-diethylaminoaniline, 4-dipropylaminoaniline, 4-[ethyl-(2-hydroxy-ethyl)amino]aniline, 4-[di(2-hydroxy-ethyl)-amino]aniline, 4-[di(2-hydroxy-ethyl)amino]-2-methyl-aniline, 4-[(2-methoxy-ethyl)amino]-aniline, 4-[(3-hydroxypropyl)amino]aniline, 4-[(2,3-hydroxypropyl)-amino]-aniline, 1,4-diamino-2-(2-hydroxyethyl)benzene, 1,4-diamino-2-(1-methyl-ethyl)-benzene, 1,3-bis[(4-aminophenyl)-(2-hydroxyethyl)amino]-2-propanol, 1,4-bis[(4-aminophenyl)-amino]butane, 1,8-bis(2,5-diaminophenoxy)-3,6-dioxa-octane, 4-aminophenol, 4-amino-3-methyl-phenol, 4-amino-3-(hydroxymethyl)-phenol, 4-amino-3-fluorophenol, 4-methylaminophenol, 4-amino-2-(amino-methyl)-phenol, 4-amino-2-(hydroxymethyl)phenol, 4-amino-2-fluoro-phenol, 4-amino-2-[(2-hydroxyethyl)amino]methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)-methyl]-1H-pyrazole, 1-[(4-chlorophenyl) methyl]-4,5-diamino-1H-pyrazole, 4,5-diamino-1-methyl-1H-pyrazole, 2-aminophenol, 2-amino-6-methylphenol and 2-amino-5-methylphenol, alone or in admixture with one another.

(ii) Couplers: N-(3-dimethylaminophenyl)urea, 2,6-diaminopyridine, 2-amino-4-[(2-hydroxy-ethyl)-amino]anisole, 2,4-diamino-1-fluoro-5-methyl-benzene, 2,4-diamino-1-methoxy-5-methyl-benzene, 2,4-diamino-1-ethoxy-5-methylbenzene, 2,4-diamino-1-(2-hydroxyethoxy)-5-methyl-benzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy) benzene, 2,4-diamino-1,5-di(2-hydroxyethoxy)benzene, 1-(2-aminoethoxy)-2,4-diamino-benzene, 2-amino-1-(2-hydroxyethoxy)-4-methylaminobenzene, 2,4-diamino-phenoxyacetic acid, 3-[di(2-hydroxyethyl)amino]aniline, 4-amino-2-di[(2-hydroxy-ethyl)-amino]-1-ethoxybenzene, 5-methyl-2-(1-methylethyl)phenol, 3-[(2-hydroxy-ethyl) amino]aniline, 3-[(2-aminoethyl)-amino]aniline, 1,3-di(2,4-diamino-phenoxy)-propane, di(2,4-diaminophenoxy)-methane, 1,3-diamino-2,4-dimethoxy-benzene, 2,6-bis(2-hydroxyethyl)aminotoluene, 4-hydroxy-indole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methyl-phenol, 3-amino-2-chloro-6-methyl-phenol, 3-amino-phenol, 2-[(3-hydroxyphenyl)-amino]acetamide, 5-[(2-hydroxy-ethyl)-amino]-4-methoxy-2-methylphenol, 5-[(2-hydroxy-ethyl)-amino]-2-methylphenol, 3-[(2-hydroxyethyl)amino]-phenol, 3-[(2-methoxyethyl)-amino]phenol, 5-amino-2-ethyl-phenol, 5-amino-2-methoxyphenol, 2-(4-amino-2-hydroxy-phenoxy)ethanol, 5-[(3-hydroxypropyl)amino]-2-methyl-phenol, 3-[(2,3-dihydroxypropyl)-amino]-2-methylphenol, 3-[(2-hydroxyethyl)amino]-2-methyl-phenol, 2-amino-3-hydroxy-pyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylene-dioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxy-indole, 6-hydroxyindole, 7-hydroxyindole and 2,3-indolinedione, alone or in admixture with one another.

(iii) Self-coupling compounds: 2-amino-5-methylphenol, 2-amino-6-methylphenol, 2-amino-5-ethoxyphenol or 2-propylamino-5-aminopyridine.

Among the aforesaid oxidation dye precursors, the following compounds, alone or in combination with one another, are particularly preferred: 2,5-diamino-toluene, 2,4-diaminophenoxyethanol, resorcinol, 2-methylresorcinol, m-aminophenol, 4-amino-m-cresol, 4-amino-2-hydroxytoluene, 6-amino-m-cresol, 2-amino-4-hydroxyethylaminoanisole, 1-naphthol, hydroxyethyl-3,4-methylene-dioxyaniline, 2,5-diaminophenylethanol, N,N-bis(2-hydroxyethyl)-p-phenylene-diamine, phenyl-methylpyrazolone, 1-hydroxyethyl-4,5-diaminopyrazole and 2-amino-6-chloro-4-nitrophenol or the salts thereof.

The total quantity of oxidation precursors present in the pellets of the invention amounts to about 0.1 to 70 weight percent and particularly about 0.5 to 50 weight percent.

To achieve certain color shades, it is also possible to use common natural and/or synthetic direct dyes, for example vegetable dyes such as henna or indigo, triphenylmethane dyes, aromatic nitro dyes, azo dyes, quinone dyes, cationic dyes or anionic dyes.

It is also possible for the pellets of the invention to contain exclusively direct dyes, namely without added oxidation precursors.

Suitable synthetic dyes are, for example: hydroxyethyl-2-nitro-p-toluidine, 2-hydroxyethylpicramic acid, 4-nitrophenylaminourea, tri(4-amino-3-methyl-phenyl)-carbenium chloride (Basic Violet 2), 1,4-diamino-9,10-anthracenedione (Disperse Violet 1), 1,4-bis[(2-hydroxyethyl)amino]-2-nitrobenzene, 1-(2-hydroxyethyl)amino-2-nitro-4-[di(2-hydroxyethyl)amino]benzene (HC Blue No. 2), 1-amino-3-methyl-4-[(2-hydroxyethyl)-amino]-6-nitrobenzene (HC Violet No. 1), 4-[ethyl-(2-hydro-xyethyl)amino]-1-[(2-hydroxy-ethyl)amino]-2-nitrobenzene hydrochloride (HC Blue No. 12), 4-[di(2-hydroxyethyl)amino]-1-[(2-methoxyethyl)-amino]-2-nitrobenzene (HC Blue No. 11), 1-[(2,3-dihydroxypropyl)-amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)-amino]-2-nitrobenzene (HC Violet No. 2), 1-methylamino-4-[methyl-(2,3-dihydroxypropyl)amino]-2-nitrobenzene (HC Blue No. 6), 2-[(4-amino-2-nitro-phenyl)amino]-5-dimethylaminobenzoic acid (HC Blue No. 13), 1-amino-4-[(2-hydroxyethyl)amino]-2-nitrobenzene (HC Red No. 7), 2-amino-4,6-dinitrophenol, 4-amino-2-nitro-diphenylamine (HC Red No. 1), 1-amino-4-[di(2-hydroxyethyl)-amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red. No. 3), 4-amino-3-nitrophenol, 4-[(2-hydroxyethyl)-amino]-3-nitrophenol, 1-[(2-aminoethyl)amino]-4-(2-hydroxyethoxy)-2-nitro-benzene (HC Orange No. 2), 4-(2,3-dihydroxypropoxy)-1-[(2-hydroxyethyl)-amino]-2-nitrobenzene (HC Orange No. 3), 1-amino-5-chloro-4-[(2,3-dihydroxy-propyl)amino]-2-nitrobenzene (HC Red No. 10), 5-chloro-1,4-[di-(2,3-dihydroxy-propyl)amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)-amino]benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitro-pyridine, 1,2,3,4-tetrahydro-6-nitroquinoxaline, 7-amino-3,4-dihydro-6-nitro-2H-1,4-benzoxazine (HC Red No. 14), 1-amino-2-[(2-hydroxyethyl)amino]-5-nitro-benzene (HC Yellow No. 5), 1-(2-hydroxyethoxy)-2-[(2-hydroxy-ethyl)-amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxy-propoxy)-3-methylamino-4-nitrobenzene, 2-[(2-hydroxy-ethyl)amino]-5-nitro-phenol (HC Yellow No. 11), 3-[(2-aminoethyl)-amino]-1-methoxy-4-nitrobenzene hydrochloride (HC Yellow No. 9), 1-[(2-ureidoethyl)amino]-4-nitrobenzene, 4-[(2,3-dihydroxypropyl)amino]-3-nitro-1-trifluoromethylbenzene (HC Yellow No. 6), 1-chloro-2,4-bis[(2-hydroxyethyl)amino]-5-nitrobenzene (HC Yellow No. 10), 4-[(2-hydroxyethyl) amino]-3-nitro-1-methylbenzene, 1-chloro-4-[(2-hydroxyethyl)-amino]-3-nitrobenzene (HC Yellow No. 12), 4-[(2-hydroxyethyl)amino]-3-nitro-1-trifluoromethyl-benzene (HC Yellow No. 13), 4-[(2-hydroxyethyl)-amino]-3-nitrobenzonitrile (HC Yellow No. 14), 4-[(2-hydroxyethyl) amino]-3-nitrobenzamide (HC Yellow No. 15), 1,4-di[(2,3-dihydroxypropyl)amino]-9,10-anthraquinone, 1-[(2-hydroxyethyl)amino]-4-methylamino-9,10-anthraquinone (C.I. 61505, Disperse Blue No. 3), 2-[(2-aminoethyl)amino]-9,10-anthraquinone (HC Orange No. 5), 1-hydroxy-4-[(4-methyl-2-sulfo-phenyl)-amino]-9,10-anthraquinone, 1-[(3-amino-propyl)amino]-4-methylamino-9,10-anthraquinone (HC Blue No. 8), 1-[(3-amino-propyl)amino]-9,10-anthraquinone (HC Red No. 8), 1,4-diamino-2-methoxy-9,10-anthraquinone (C. I. 62015, Disperse Red No. 11, Solvent Violet No. 26), 1,4-dihydroxy-5,8-bis-[(2-hydroxyethyl) amino]-9,10-anthraquinone (C.I. 62500, Disperse Blue No. 7, Solvent Blue No. 69), 9-(dimethylamino)benzo[a]-phenoxazin-7-ium chloride (C.I. 51175; Basic Blue No. 6), di[4-(diethylamino)-phenyl][4-(ethylamino)naphthyl]-carbenium chloride (C.I. 42595; Basic Blue No. 7), 3,7-di (dimethylamino)phenothiazin-5-ium chloride (C.I. 52015; Basic Blue No. 9), di[4-(dimethylamino)phenyl][4-phenylamino)-naphthyl]carbenium chloride (C.I. 44045; Basic Blue No. 26), 2-[(4-(ethyl-(2-hydroxyethyl)-amino)phenyl) azo]-6-methoxy-3-methyl-benzothiazolium methylsulfate (C.I. 11154; Basic Blue No. 41), 8-amino-2-bromo-5-hydroxy-4-imino-6-{[(3-trimethylammonio)phenyl]-amino}-1 (4H)-naphthalenone chloride (C.I. 56059; Basic Blue No. 99), bis-[4-(dimethylamino)-phenyl][4-(methylamino)phenyl]carbenium chloride (C.I. 42535; Basic Violet No. 1), tris-[4-(dimethylamino)phenyl]carbenium chloride (C.I. 42555; Basic Violet No. 3), 2-[3,6-(diethylamino)dibenzopyranium-9-yl]-benzoyl chloride (C.I. 45170; Basic Violet No. 10), di(4-aminophenyl)-(4-amino-3-methylphenyl)-carbenium chloride (C.I. 42510; Basic Violet No. 14), 1,3-bis-[(2, 4-diamino-5-methylphenyl)azo]-3-methylbenzene (C.I. 21010; Basic Brown No. 4), 1-[(4-aminophenyl)azo]-7-(trimethylammonio)-2-naphthol chloride (C.I. 12250; Basic Brown No. 16), 1-[(4-amino-2-nitro-phenyl)azo]-7-(trimethylammonio)-2-naphthol chloride (Basic Brown No. 17), 1-[(4-amino-3-nitrophenyl)azo]-7-(trimethyl-ammonio)-2-naphthol chloride (C.I. 12251; Basic Brown No. 17), 3,7-diamino-2,8-dimethyl-5-phenylphenazinium chloride (C.I. 50240; Basic Red. No. 2), 1,4-dimethyl-5-{[4-(dimethylamino)phenyl]azo}-1,2,4-triazolium chloride (C.I. 11055; Basic Red No. 22), 2-hydroxy-1-[(2-methoxyphenyl)azo]-7-(trimethyl-ammonio)-naphthalene chloride (C.I. 12245; Basic Red No. 76), 2-{2-[(2,4-dimethoxy-phenyl)-amino] ethenyl}-1,3,3-trimethyl-3H-indol-1-ium chloride (C.I. 48055; Basic Yellow No. 11), 3-methyl-1-phenyl-4-{[3-(trimethylammonio)phenyl]azo}pyrazol-5-one chloride (C.I. 12719; Basic Yellow No. 57), bis-[4-(diethylamino)phenyl]-phenylcarbenium hydrogen sulfate (1:1) (C.I. 42040; Basic Green No. 1), 1-[di-(2-hydroxyethyl)amino]-3-methyl-4-[(4-nitrophenyl)azo]benzene (C.I. 11210, Disperse Red No. 17), 4-[(4-aminophenyl)azo]-1-[di-(2-hydroxyethyl)amino]-3-methylbenzene (HC Yellow No. 7), 2,6-di-amino-3-[(pyridin-3-yl)-azo]pyridine, disodium 6-hydroxy-5-[(4-sulfophenyl)-2-naphthalene sulfonate (C.I. 15985; Food Yellow No. 3; FD&C Yellow No. 6), disodium 2,4-dinitro-1-naphthol-7-sulfonate (C.I. 10316; Acid Yellow No. 1; Food Yellow No. 1), 2-(indan-1,3-dion-2-yl)-quinolin-x,x-sulfonic acid (mixture of mono- and disulfonic acid) (C.I. 47005; D&C Yellow No. 10; Food Yellow No. 13; Acid Yellow No. 3), trisodium 5-hydroxy-1-(4-sulfophenyl)-4-[(4-sulfophenyl)azo]pyrazole-3-carboxylate (C.I. 19140; Food Yellow No. 4; Acid Yellow No. 23), 9-(2-carboxyphenyl)-6-hydroxy-3H-xanthen-3-one (C.I. 45350; Acid Yellow No. 73; D&C Yellow No. 8), sodium 5-[(2,4-dinitrophenyl)amino]-2-phenylaminobenzene sulfonate (C.I. 10385; Acid Orange No. 3), monosodium 4-[(2,4-dihydroxyphenyl)-azo]benzene sulfonate (C.I. 14270; Acid Orange No. 6), sodium 4-[(2-hydroxynaphth-1-yl)azo]-benzene sulfonate (C.I. 15510; Acid Orange No. 7), sodium 4-[(2,4-dihydroxy-3-[(2,4-dimethylphenyl)azo]phenyl)-azo]-benzene sulfonate (C.I. 20170; Acid Orange No. 24), disodium 4-hydroxy-3-[(4-sulfonaphth-1-yl)-azo]-1-naphthalene sulfonate (C.I. 14720; Acid Red No. 14), trisodium 6-hydroxy-5-[(4-sulfonaphth-1-yl)azo]-2,4-naphthalenedisulfonate (C.I. 16255; Ponceau 4R; Acid Red No. 18), trisodium 3-hydroxy-4-[(4-sulfonaphth-1-yl)-azo]-2,7-naphthalene disulfonate (C.I. 16185; Acid Red No. 27), disodium 8-amino-1-hydroxy-2-(phenylazo)-3,6-naphthalene disulfonate (C.I. 17200; Acid Red No. 33), disodium 5-(acetyl-amino)-4-hydroxy-3-[(2-methylphenyl)azo]-2,7-naphthalene disulfonate (C.I. 18065; Acid Red No. 35), disodium 2-(3-hydroxy-2,4,5,7-tetra-iododibenzopyran-6-on-9-yl)benzoate (C.I. 45430; Acid Red No. 51), N-[6-(diethylamino)-9-(2,4-disulfophenyl)-3H-xanthen-3-ylidene]-N-ethylethaneammoium hydroxide inner salt, sodium salt (C.I. 45100; Acid Red No. 52), disodium 8-{[4-(phenylazo)-phenyl]azo}-7-naphthol-1,3-disulfonate (C.I. 27290; Acid Red No. 73); 2',4',5',7'-tetrabromo-3',6'-dihydroxyspiro{isobenzofuran-1(3H), 9'-[9H]xanthen}-3-one disodium salt (C.I. 45380; Acid Red No. 87), 2',4',5',7'-tetrabromo-4,5,6,7-tetra-chloro-3',6'-dihydroxyspiro-{isobenzofuran-1-3H), 9'[9H]-xanthen}-3-one disodium salt (C.I. 45410; Acid Red No. 92), 3',6'-dihydroxy-4',5'-diiodospiro{isobenzofuran-1(3H), 9(9H)-xanthen}-3-one disodium salt (C.I. 45425; Acid Red No. 95), (2-sulfophenyl)-di[4-(ethyl((4-sulfo-phenyl)methyl)amino)-phenyl]-carbenium disodium salt, betaine (C.I. 42090; Acid Blue No. 9; FD&C Blue No. 1), 1,4-bis[(2-sulfo-4-methylphenyl)amino]-9,10-anthraquinone disodium salt (C.I. 61570; Acid Green No. 25), bis[4-(dimethyl-amino)phenyl]-(3,7-disulfo-2-hydroxy-naphth-1-yl)-carbenium inner salt, monosodium salt (C.I. 44090; Food Green No. 4; Acid Green No. 50), bis-[4-(diethylamino)phenyl]-(2,4-di-sulfophenyl)-carbenium inner salt, sodium salt (2:1) (C.I. 42045; Food Blue No. 3; Acid Blue No. 1), bis[4-[diethylamino)phenyl](5-hydroxy-2,4-disulfophenyl)-carbenium inner salt, calcium salt (2:1) (C.I. 42051; Acid Blue No. 3), sodium 1-amino-4-(cyclohexyl-amino)-9,10-anthraquinone-2-sulfonate (C.I. 62045; Acid Blue No. 62), disodium 2-(1,3-dihydro-3-keto-5-sulfo-2H-indol-2-ylidene)-2,3-dihydro-3-keto-1H-indol-5-sulfonate (C.I. 73015; Acid Blue No. 74), 9-(2-carboxyphenyl)-3-[(2-methylphenyl)amino]-6-[(2-methyl-4-sulfophenyl)-amino]-xanthylium inner salt, monosodium salt (C.I. 45190; Acid Violet No. 9), 1-hydroxy-4-[(4-methyl-2-sulfo-phenyl)amino]-9,10-anthraquinone sodium salt (C.I. 60730; D&C Violet No. 2; Acid Violet No. 43), bis{3-nitro-4-[(4-phenylamino)-3-sulfo-phenylamino]phenyl}sulfone (C.I. 10410; Acid Brown No. 13), disodium 5-amino-4-hydroxy-6-[(4-nitro-phenyl)azo]-3-(phenylazo)-2,7-naphthalene disulfonate (C.I. 20470; Acid Black No. 1), 3-hydroxy-4-[(2-hydroxynaphth-1-yl)azo]-7-nitro-1-naphthalene sulfonic acid chromium complex (3:2) (C.I. 15711); Acid Black No. 52), disodium 3-[(2,4-dimethyl-5-sulfophenyl)azo]-4-hydroxy-1-naphthalene sulfonate (C.I. 14700; Food Red No. 1; FD&C Red No. 4), tetrasodium 4-(acetylamino)-5-hydroxy-6-[(7-sulfo-4-[(4-sulfo-phenyl)azo]naphth-1-yl)azo]-1,7-naphthalene disulfonate (C.I. 28440; Food Black No. 1) and sodium 3-hydroxy-4-(3-methyl-5-keto-1-phenyl-4,5-dihydro-1H-pyrazol-4-yl-azo)-naphthalene-1-sulfonate, chromium complex (Acid Red No. 195), 3',3",4,5,5',5",6,7-octabromophenol-sulfonphthalein (Tetrabromophenol Blue), 1-((4-amino-3,5-dimethyl-phenyl)-(2,6-dichlorophenyl)-methylene)-3,5-dimethyl-4-imino-2,5-cyclohexadiene combined with phosphoric acid (1:1) (Basic Blue 77), 2',4',5',7'-tetrabromo-4,5,6,7-tetrachloro-3',6'-dihydroxyspiro{isobenzofuran-1-(3H), 9'[9H]-xanthen}-3-one disodium salt (Acid Red No. 92), N,N-di(2-hydroxyethyl)-3-methyl-4-[(4-nitrophenyl)azo]-aniline (Disperse Red 17), disodium 2,4-dinitro-1-naphthol-7-sulfonate (Acid Yellow 1), sodium 4-[(2-hydroxynaphthalen-1-yl)-azo]-benzene sulfonate (Acid Orange 7), 2-((4-(ethyl-(2-hydroxyethyl)amino)-2-methylphenyl)azo)-5-nitro-1,3-thiazole (Disperse Blue 106), 2,4-dinitro-1-naphthol, 2-[(4-aminophenyl)azo]-1,3-dimethyl-1H-imidazol-3-ium chloride, 1-methyl-4-[(methylphenyl-hydrazono)-methyl]pyridinium methosulfate, 2-{[4-(dimethyl-amino)phenyl]azo}-1,3-dimethyl-imidazolium chloride, 2-((4-((4-methoxyphenyl)amino)-phenyl)azo)-1,3-dimethyl-1H-imidazol-3-ium chloride and 1,3-dimethyl-2-((4-((phenyl-methyl)amino)-phenyl)-azo)-1H-imidazol-3-ium chloride, alone or in combination with one another.

Particularly preferred among the aforesaid direct dyes are the following compounds, alone or in combination with one another: hydroxyethyl-2-nitro-p-toluidine, 2-hydroxyethylpicramic acid, 4-nitrophenylaminourea, tri(4-amino-3-methylphenyl)-carbenium chloride (Basic Violet 2), 1,4-diamino-9,10-anthracenedione (Disperse Violet 1), 1-(2-hydroxyethyl)amino-2-nitro-4-[di(2-hydroxyethyl)amino] benzene (HC Blue No. 2), 4-[ethyl-(2-hydroxyethyl)amino]-1-[(2-hydroxy-ethyl)amino]-2-nitrobenzene hydrochloride (HC Blue No. 12), 1-amino-4-[di(2-hydroxyethyl)-amino]-2-nitrobenzene hydrochloride (HC Red No. 13), 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-chloro-6-ethylamino-4-nitro-phenol, 2-amino-6-chloro-4-nitrophenol, 4-[(2-hydroxyethyl)amino]-3-nitro-1-trifluoromethyl-benzene (HC Yellow No. 13), 8-amino-2-bromo-5-hydroxy-4-imino-6-{[3-(trimethylammonio)-phenyl]amino}-1(4H)-naphthalenone chloride (C.I. 56059; Basic Blue No. 99), 1-[(4-amino-phenyl)azo]-7-(trimethylammonio)-2-naphthol chloride (C.I. 12250; Basic Brown No. 16), 1-[(4-amino-2-nitrophenyl)-azo]-7-(trimethylammonio)-2-naphthol chloride (Basic Brown No. 17), 2-hydroxy-1-[(2-methoxyphenyl)azo]-7-(trimethylammonio)naphthalene chloride (C.I. 12245; Basic Red No. 76), 3-methyl-1-phenyl-4-{[3-(trimethylammonio)-phenyl]azo}-pyrazol-5-one chloride (C.I. 12719; Basic Yellow No. 57) and 2,6-diamino-3-[(pyridin-3-yl)azo]pyridine as well as the salts thereof.

The total quantity of direct dyes in the pellets of the invention amounts to about 0.1 to 90 weight percent and preferably 1 to 70 weight percent.

Other known and common dyes used in hair colorants are described in, among other publications, E. Sagarin "Cosmetics, Science and Technology", Interscience Publishers Inc., New York (1957), pages 503 ff, in H. Janistyn, "Handbuch der Kosmetika und Riechstoffe" [Manual of Cosmetics and Fragrances], vol. 3 (1973), pages 388 if, and in K. Schrader "Grundlagen und Rezepturen der Kosmetika" [Fundamentals and Formulations of Cosmetics], 2nd edition (1989), pages 782-815, the disclosures of which are hereby incorporated herein by reference.

The dye-containing pellets of the invention have many advantages. They are absolutely dust-free, but do not have the drawbacks presented by the common dust-free, oil-treated powders and, in particular, do not exert an adverse effect on product performance. Depending on the kind and layer thickness of the selected coating material, the release of the dyes is possible at any desired point in time (delayed release). Also possible is the use of reactive dyes together with reactive raw materials (for example oxidants such as the persulfates and hydrogen peroxide salts or hydrogen peroxide addition products) as well as a clearly improved storage stability compared to powders and aqueous/alcoholic systems. Of particular interest is the possibility of uncomplicated achievement of multicolor effects through the kind and layer thickness of the selected coating material, whereas according to the current state of the art such multicolor effects can be attained only by extremely time-consuming and complicated techniques, for example by sheet or strand techniques. In addition, the pellets of the invention have clearly better dosability than do prior-art colorants (powders, aqueous/alcoholic systems).

Other objects of the present invention therefore are the use of the aforesaid pellets for producing colorants for keratin fibers and an agent for coloring keratin fibers, for example hair and particularly human hair, which is prepared by mixing the aforesaid pellets with an aqueous or aqueous-alcoholic preparation.

The aqueous or aqueous-alcoholic preparation used can be either water or a mixture of water and a $C_1$-$C_6$-alcohol (for example, ethanol or isopropanol) or a common hydrogen peroxide solution or hydrogen peroxide emulsion or else a common hair cleaning agent, hair conditioner or hair-firming agent.

The composition of such preparations is known and can be found in pertinent textbooks on cosmetics, for example in Karlheinz Schrader "Grundlagen und Rezepturen der Kosmetika" [Fundamentals and Formulations of Cosmetics], 2nd edition (1989), which is hereby incorporated herein by reference.

For example, the colorant of the invention can contain antioxidants, for example ascorbic acid, thioglycolic acid or sodium sulfite, as well as complexing agents for heavy metals, for example an ethylenediaminetetraacetate or nitriloacetic acid, in an amount of up to about 0.5 weight percent. Perfume oils can be contained in the dye carrier composition of the invention in an amount of up to about 1 weight percent. Moreover, the afore-described hair colorant can optionally contain other auxiliary agents and additives commonly used in such colorants, for example thickeners, for example homopolymers of acrylic acid, vegetable gums, algal polysaccharides, amphiphilic associative thickeners; furthermore preservatives; complexing agents; wetting agents or emulsifiers from the classes of anionic, cationic, amphoteric or nonionic surface-active substances; alkalizing agents (for example ammonium salts, or amino acids such as glycine and alanine) furthermore hair-care agents, such as cationic polymers or resins, lanolin derivatives, cholesterol, vitamins, pantothenic acid and betaine. The said constituents are employed in amounts normally used for such purposes, for example the wetting agents and emulsifiers at a concentration from 0.1 to 30 weight percent and the hair-care agents at a concentration from 0.1 to 5.0 weight percent.

The colorants containing oxidation dye precursors are used in combination with one or more known chemical oxidants, for example hydrogen peroxide or a salt or adduct thereof, as well as persulfates such as sodium persulfate, potassium persulfate or ammonium persulfate, or they are activated by air oxidation (optionally in the presence of appropriate enzymes or catalysts). If simultaneous brightening and coloring of the fibers is desired, it is also possible to use colorants based on direct dyes—provided said dyes are sufficiently oxidation-resistant—in combination with one or more known oxidants, for example hydrogen peroxide or a salt or adduct thereof as well as persulfates such as sodium persulfate, potassium persulfate or ammonium persulfate.

To attain simultaneous brightening of the fibers, the dye-containing pellets of the invention can also contain an ammonium carbonate, for example ammonium hydrogen carbonate, or an amino acid or a salt thereof, for example sodium glycinate.

The following examples will explain the subject matter of the invention in greater detail without limiting its scope to these examples.

EXAMPLES

Example 1

Preparation of Dye Pellets by the Top Spray Method

In a Glatt fluidized bed granulator and coater, the following mixture A was heated to a product temperature of 34° C. with air at an incoming air temperature of 90° C. and an air flow rate of 18 m³/h.

| Mixture A | |
|---|---|
| 381.2 g | of 4-(2-hydroxyethylamino)-3-nitrophenol |
| 101.0 g | of 2-[(2-hydroxyethyl)amino]-4,6-dinitrophenol |
| 100.0 g | of corn starch |

A 20% aqueous polyvinylpyrrolidone solution ("spraying solution") was then sprayed onto this mixture at an initial spraying rate of 8 g/min and at a spraying air pressure of 0.5 bar. In the course of the granulation process, the spraying rate was increased to 12 g/min and the incoming air temperature was increased to 100° C., while the air flow rate was raised to a maximum of 30 m³/h. The product temperature was kept at about 30-31° C. throughout the entire procedure. After 310 g had been sprayed on, the pellets were dried at a maximum product temperature of 57° C. and then cooled to about 30° C. and screened.

Example 2

Preparation of Dye Pellets by Extruder Technology

| Mixture A | |
|---|---|
| 1896 g | of 4-(2-hydroxyethylamino)-3-nitrophenol |
| 504 g | of 2-[(2-hydroxyethyl)amino]-4,6-dinitrophenol |
| 800 g | of microcrystalline cellulose |
| 800 g | of corn starch |

Mixture A was mixed in a vertical granulator (rotor rotational speed=about 150 rpm; chopper rotational speed=about 1000 rpm) for 1 minute and then, by means of a dual nozzle and with continuing mixing, sprayed with 2091 g of a 6% aqueous hydroxypropyl methylcellulose solution. The composition thus obtained was extruded from a BR 200-type extruder (rotational speed=27 rpm; screen mesh diameter: 1.0 mm) at a product temperature of about 30° C. The material thus obtained was then rounded in a P 50-type pelletizer for 1 minute at 550 rpm and then dried in a Glatt vertical granulator at an incoming air temperature of 70° C., an air flow rate of about 60-90 m³/h and a maximum product temperature of 51° C.

In a Glatt fluidized bed granulator and coater, 1500 g of the dried dye pellets was heated at an incoming air temperature of about 50° C. and an air flow rate of 75 m³/h to a product temperature of 39-40° C. The pellets were then sprayed with a 10% aqueous solution of hydroxypropylmethyl cellulose at a spraying rate of 5 g/min and a spraying air pressure of 2.5 bar. In the course of the procedure, the spraying rate was increased to 8.5 g/min. After 2215 g of the spraying solution had been applied, corresponding to an addition of 14% of solids, the material was again dried at a maximum product temperature of 51° C. (incoming air temperature=about 70° C.), and then cooled to about 27° C. and screened.

(Alternatively the drying and coating or the granulation, drying and coating can be carried out in the same processing step).

Example 3

Preparation of Dye Pellets by Extruder Technology; Gold Color Shade

| Mixture A | |
|---|---|
| 2400 g | of 2-amino-6-chloro-4-nitrophenol |
| 800 g | of microcrystalline cellulose |
| 800 g | of corn starch |

Mixture A was pelletized as in Example 2, but by using a 5.6% aqueous hydroxypropyl-methylcellulose solution as the coating agent.

Example 4

Preparation of Dye Pellets by Extruder Technology; Red/Mahogany Color Shade

| Mixture A | |
|---|---|
| 1896 g | of 3-nitro-p-hydroxyethylaminophenol |
| 504 g | of 2-hydroxyethylpicramic acid |
| 800 g | of microcrystalline cellulose |
| 800 g | of potato starch |

The preparation was carried out as described in Example 2, but by using a 6.25% aqueous hydroxymethylcellulose solution as the coating agent.

Example 5

Preparation of Dye Pellets by Extruder Technology

| Mixture A | |
|---|---|
| 1411 g | of 2,5-diaminotoluene sulfate |
| 636 g | of 4-amino-2-hydroxytoluene |
| 353 g | of 2-amino-4-(β-hydroxyethylamino)anisole sulfate |
| 794 g | of ascorbic acid |
| 1058 g | of sodium sulfite |
| 800 g | of hydroxypropyl cellulose |
| 1300 g | of corn starch |

The preparation was carried out as described in Example 2, but by using a 5.625% aqueous hydroxypropylmethyl cellulose solution as the coating agent.

Example 6

Preparation of Dye Pellets by the Top Spray Method

| Mixture A | |
|---|---|
| 7.2 g | of 5-amino-2-methylphenol |
| 16.0 g | of 2,5-diaminotoluene sulfate |
| 4.0 g | of 2-amino-4-(β-hydroxyethylamino)anisole sulfate |
| 3.0 g | of ascorbic acid |
| 4.0 g | of sodium sulfite |
| 965.8 g | of hydrolyzed corn starch (oligosaccharide) |

The mixture was pelletized as described in Example 1 with 563 g of a 20% aqueous polyvinyl-pyrrolidone solution.

Example 7

Preparation of Dye Pellets by the Top Spray Method

| Mixture A: | 879 g | of dextrose |
|---|---|---|
| Mixture B: | 30 g | of 2-amino-6-chloro-4-nitrophenol |
| (dispersion) | 500 g | of a 20% aqueous polyvinyl-pyrrolidone solution (mol. wt. = 30,000 g/mol) |

The mixture was pelletized as described in Example 1, but by using the afore-described mixture (B) as spraying solution.

Example 8

Preparation of Dye Pellets by the Top Spray Method

| Mixture A: | 693.7 g | of dextrose |
|---|---|---|
| Mixture B: | 20.8 g | of 4-(β-hydroxyethylamino)-3-nitrophenol |

-continued

| | | |
|---|---|---|
| (dispersion) | 5.5 g | of 2-hydroxyethylpicramic acid |
| | 400.0 g | of 20% aqueous polyvinylpyrrolidone solution (mol. wt. = 30,000 g/mol) |

The mixture was pelletized as described in Example 1, but by using the afore-described mixture (B) as spraying solution.

Example 9

Preparation of Dye Pellets by the Top Spray Method

| | | |
|---|---|---|
| Mixture A: | 721.6 g | of dextrose |
| Mixture B: | 17.0 g | of 2,5-diaminotoluene sulfate |
| (dispersion) | 2.0 g | of resorcinol |
| | 7.6 g | of 2-methylresorcinol |
| | 2.2 g | of 2-amino-6-chloro-4-nitrophenol |
| | 2.4 g | of 6-amino-m-cresol |
| | 0.2 g | of 4-amino-2-hydroxytoluene |
| | 3.0 g | of ascorbic acid |
| | 4.0 g | of sodium sulfite |
| | 80.0 g | of alanine |
| | 60.0 g | of glycine |
| | 500.0 g | of 20% aqueous polyvinylpyrrolidone solution (mol. wt. = 30,000 g/mol) |

Mixture (A) was pelletized as described in Example 1, but by using the afore-described mixture (B) as spraying solution.

Example 10

Creamy Hair Colorant

| Cream base | |
|---|---|
| 8.70 g | of cetylstearyl alcohol |
| 2.30 g | of glyceryl stearate (self-emulsifying) |
| 0.80 g | of lanolin |
| 3.80 g | of lanolin alcohol |
| 1.42 g | of sodium cetylstearyl sulfate |
| 0.07 g | of formaldehyde |
| 0.01 g | of tocopherol |
| 0.20 g | of perfume |
| 10.00 g | of ammonia |
| to 100.00 g | water |

The afore-described cream base was prepared by the conventional hot-emulsification method. Before use, it was mixed with the dye pellets in an appropriate ratio as in one of Examples 1, 2, 3, 7, or 8 in a dye cup or shaking bottle.

Example 11

Oxidation Hair Colorant

| Hydrogen Peroxide Emulsion | |
|---|---|
| 9.00 g | of hydrogen peroxide |
| 1.80 g | of cetylstearyl alcohol |
| 3.30 g | of polyvinylpyrrolidone-styrene copolymer |
| 0.20 g | of disodium phosphate |

-continued

| Hydrogen Peroxide Emulsion | |
|---|---|
| 0.20 g | of sodium laurylsulfate |
| 0.10 g | of salicylic acid |
| 0.08 g | of phosphoric acid |
| to 100.00 g | water |

The above-described hydrogen peroxide emulsion was prepared by the conventional hot-emulsification method. Just before use, this hydrogen peroxide emulsion was mixed with dye pellets as in Example 5, 6 or 9 in a dye cup or a shaking flask.

Unless otherwise indicated, all percentages are by weight.

The invention claimed is:

1. A coated dye-containing pellet comprising a granulated carrier material and a coating material that encapsulates the granulated carrier material;
   wherein said coating material comprises a mixture of an encapsulating material with at least one natural and/or synthetic dye;
   wherein said at least one natural and/or synthetic dye comprises 1 to 70 wt. % of at least one direct dye and 0.5 to 50 wt. % of at least one oxidation dye precursor; and
   wherein said coated dye-containing pellet comprises at least one antioxidant selected from the group consisting of ascorbic acid, thioglycolic acid and sodium sulfite.

2. The coated dye-containing pellet as defined in claim 1, containing from 0.50 to 50 wt. % of said encapsulating material, based on a total amount of said granulated carrier material present.

3. The coated dye-containing pellet as defined in claim 1, containing from 1 to 20 wt. % of said encapsulating material, based on a total amount of said granulated carrier material present.

4. The coated dye-containing pellet as defined in claim 1, wherein said granulated carrier material is a granulate of a substance, which is selected from the group consisting of polyvinyl pyrrolidones, dextrose, oligosaccharides, microcrystalline cellulose derivatives, physically modified starches, chemically modified starches, physically modified starch derivatives, chemically modified starch derivatives, synthetic calcium silicate, diatomite, silicon dioxide and free-flowing non-baking powders.

5. The coated dye-containing pellet as defined in claim 1, wherein said encapsulating material is a water-soluble or water-dispersible film-forming polymeric substance which, when spray-dried from a solution or a dispersion, is capable of depositing a uniform film.

6. The coated dye-containing pellet as defined in claim 5, wherein said water-soluble or water-dispersible film-forming polymeric substance is selected from the group consisting of cellulose polymers, polyethylene dispersions, polyacrylic acids, polyvinyl alcohols, polyvinyl pyrrolidones, polycarbonates, polyesters, polyamides and natural film-forming polymers.

7. The coated dye-containing pellet as defined in claim 6, wherein said natural film-forming polymers include chitosan, shellac, oligosaccharides and colophony.

8. The coated dye-containing pellet as defined in claim 1, wherein said at least one natural and/or synthetic dye comprises at least one direct dye and said at least one direct dye is selected from the group consisting of hydroxyethyl-2-nitro-p-toluidine, 2-hydroxyethylpicramic acid, 4-nitrophenylaminourea, Basic Violet 2, Disperse Violet 1, HC Blue No. 2, HC Blue No. 12, HC Red No. 13, HC Red No. 3,4-amino-3- nitrophenol, 4-[(2-hydroxy-ethyl)amino]-3-nitrophenol, HC Red No. 10, HC Red No. 11,2-chloro-6-ethyl-amino-4-nitrophenol, HC Yellow No. 13, Basic Blue No. 99 Basic Brown No. 16, Basic Brown No. 17, Basic Red No. 76, Basic Yellow No. 57, 2,6-diamino-3-[(pyridin-3-yl)azo]-pyridine and salts thereof.

9. The coated dye-containing pellet as defined in claim 1, wherein said at least one natural and/or synthetic dye comprises at least one oxidation dye precursor and said at least one oxidation dye precursor is selected from the group consisting of 2,5-diaminotoluene, 2,4-diaminophenoxy-ethanol, resorcinol, 2-methylresorcinol, m-aminophenol, 4-amino-m-cresol, 4-amino-2-hydroxytoluene, 6-amino-m-cresol, 2-amino-4-hydroxyethylamino-an sole, 1-naphthol, hydroxyethyl-3,4-methylenedioxyaniline, 2,5-diaminophenyl-ethanol, N,N-bis-(2-hydroxyethyl)-p-phenylenediamine, phenylmethylpyrazolone, 1-hydroxyethyl-4,5-diamino-pyrazole, 2-amino-6-chloro-4-nitrophenol and salts thereof.

10. The coated dye-containing pellet as defined in claim 1, which is made by a process in which a carrier material is granulated together with optional antioxidants and optionally auxiliary agents in a fluidized bed granulator/coater to form said granulated carrier material at room temperature, said granulated carrier material is heated at a temperature of no more than 34° C., subsequently said granulated carrier material is coated by spraying with a solution or dispersion of said coating material and optionally drying as needed.

11. A coated dye-containing pellet comprising a granulated carrier material and a coating material that encapsulates the granulated carrier material;
   wherein said coating material comprises a mixture of an encapsulating material with at least one natural and/or synthetic dye;
   wherein said at least one natural and/or synthetic dye comprises 1 to 70 wt. % of at least one direct dye and 0.5 to 50 wt. % of at least one oxidation dye precursor; and
   wherein said coated dye-containing pellet comprises at least one auxiliary agent selected from the group consisting of thickeners, preservatives, complexing agents, wetting agents, emulsifiers, alkalizing agents, perfume oils and hair-care agents.

* * * * *